(12) United States Patent
Minter et al.

(10) Patent No.: US 6,660,141 B1
(45) Date of Patent: Dec. 9, 2003

(54) ELECTROCHEMICAL SENSOR

(75) Inventors: Stephen Minter, High Peak (GB); Timothy Minter, High Peak (GB)

(73) Assignee: Moorlodge Ventures Limited, High Peak (GB)

( * ) Notice: Subject to any disclaimer, the term of this patent is extended or adjusted under 35 U.S.C. 154(b) by 0 days.

(21) Appl. No.: 09/856,809

(22) PCT Filed: Nov. 26, 1999

(86) PCT No.: PCT/GB99/03920
§ 371 (c)(1),
(2), (4) Date: Oct. 1, 2001

(87) PCT Pub. No.: WO00/33063
PCT Pub. Date: Jun. 8, 2000

(30) Foreign Application Priority Data

Nov. 28, 1998 (GB) .............................................. 9825992

(51) Int. Cl.$^7$ ........................ G01N 27/30; G01N 27/327
(52) U.S. Cl. ............. 204/400; 204/403.01; 204/403.15; 204/403.16; 204/409
(58) Field of Search ....................... 204/403.01, 403.15, 204/416, 409, 400

(56) References Cited

U.S. PATENT DOCUMENTS 5,909,114 A * 6/1999 Uchiyama et al. ............ 324/94

FOREIGN PATENT DOCUMENTS

WO 9506240 A * 3/1995

OTHER PUBLICATIONS

JPO abstract of JP 61–167854 A (Akira).*

\* cited by examiner

*Primary Examiner*—T. Tung
*Assistant Examiner*—Alex Noguerola
(74) *Attorney, Agent, or Firm*—Woodard, Emhardt, Moriarty, McNett & Henry LLP

(57) ABSTRACT

The present invention relates to an electrochemical sensor for a liquid sample. The sensor comprises a substrate (1) along which a liquid may travel by capillary action, said substrate being associated with an electrochemical detection arrangement (3) and a power source therefor, wherein the power source comprises at least one pair of electrodes (7, 8) of dissimilar material provided on the substrate and arranged such that liquid travel between the electrodes causes a current to be generated for operating the electrochemical detection arrangement.

9 Claims, 1 Drawing Sheet

ELECTROCHEMICAL SENSOR

The invention relates to electrochemical sensors for determining the presence of a species in a liquid sample.

Sensors are used generally in the field of science to test and monitor the presence or levels of a species in a liquid sample. Liquid samples that may be tested include biological samples such as blood or urine samples, to determine levels of a particular analyte associated with a disease state or water or dissolved soil samples to look for the presence of particular metals or pollutants.

In many cases, samples from the body or from soil or water are taken to a laboratory for testing. In such situations, the sensor apparatus may be of any size and be powered by a mains power source. However, in some cases it is desirable to monitor a sample "in situ", or immediately after a sample has been taken, reducing the likelihood of a sample degrading before being tested. This is particularly important when testing biological samples or potentially radioactive samples, due to the potential for degradation of the species under test. It is therefore desirable to provide a portable sensor. Furthermore, it is also desirable to provide a hand-held sensor which may readily be used by an unskilled person in a non-laboratory setting such as at home, at a doctor's surgery or clinic. This is especially important when testing biological samples, for example for testing for a biological condition.

According to the present invention there is provided an electrochemical sensor for a liquid sample, the sensor comprising a substrate along which a liquid may travel by capillary action, said substrate being associated with an electrochemical detection arrangement and a power source therefor, wherein the power source comprises at least one pair of electrodes of dissimilar material provided on the substrate and arranged such that liquid travel between the electrodes causes a current to be generated for operating the electrochemical detection arrangement.

The present invention thus provides an electrochemical sensor that has its own integral power source. When liquid is applied to the sensor it will tend to be drawn along the substrate by capillary action and will moisten the previously dry substrate, allowing current to be generated by the power source.

Examples of materials from which the electrodes may be made include carbon, gold, silver, copper, tin, lead, iron and zinc. Most preferred arrangement has alternating copper and zinc electrodes.

In a preferred arrangement according to the present invention the electrodes comprises a plurality of fingers arranged such that the electrodes of one material are interdigitated with those electrodes of another dissimilar material such that current, in the presence of liquid, may flow from one electrode to another.

This preferred arrangement provides a sensor with increased power, in that the more fingers there are the more power is provided to the sensor.

In this arrangement the amount of current generated by the power source is dependent upon the length of travel of the liquid sample along the substrate and the nature and amount of the electrolyte in the sample under test. For example, if the sample is water from a fresh-water lake, the power generated for a particular length of sample travel along the substrate will be low as compared to the power generated by the same length of travel as a sea water sample, with a higher salt content and therefore higher ionic strength. In certain circumstances, when samples of low ionic strength are being tested it is advantageous to pre-apply extra electrolyte to the substrate. This "spiking" of the substrate allows the power source to work even when testing samples containing electrolytes of low ionic strength.

According to a preferred embodiment the sensor comprises a first liquid travel track (the "power track") provided over at least part of its length with a power source formed of interdigitated electrodes of dissimilar materials, and a second liquid travel track (the "analysis track") provided at its downstream end with a detection electrode arrangement associated with the electrochemical detection arrangement.

According to one embodiment, the power track is arranged such that sufficient power is generated for the electrochemical detection arrangement when sufficient liquid has travelled along the assay track for the liquid to reach the detection electrodes.

It is preferred that in this arrangement that the two liquid travel tracks are discrete and are separated by a liquid impermeable barrier.

In another preferred arrangement the sensor further comprises a sample application region in fluid communication with the liquid travel track(s). Preferably the sample application region is an absorbent pad.

In order to provide an improved device a third travel track may be provided to acts as a control against which to compare the assay track results to take account of any artefacts in the liquid sample which may affect the level of label detected by the electrochemical detection arrangement.

The electrochemical sensor may further comprise indicator means to display test results. Preferably. the indicator means incorporates an electronic circuit that interprets the output of the electrochemical detection arrangement and provides a specific signal at the indicator means depending upon the test results. Preferably the electronic circuit is a logic circuit. It is also envisaged that an amplifier circuit may also be used.

The signal at the indicator means may be clearly visible or may alternatively be audible. Suitable indicator means include liquid crystals or light emitting diode displays.

The signal generated at the indicator means may show that the test is positive for a species, negative for the species or that the sensor is not yet ready, in that not enough liquid sample has reached the detection electrodes. A preferred indicator means is a "traffic light" signal, whereby a positive test result is indicated by a green signal, a negative test result is indicated by a red signal and an inconclusive test is indicated by an amber or orange signal. Alternatively, the indicator means provides a text message and further means to indicate that the sensor is sufficiently powered.

If an inconclusive result is shown on the indicator means this may be due to either insufficient liquid being applied to the substrate so that not enough power will not be generated at the electrochemical detection arrangement and therefore the sensor will not be able to run, or that although the sensor is working insufficient travel of the sample liquid along the assay track has occurred for the liquid to reach the detection electrodes.

By providing the sensor with additional indicator means can clearly show that sufficient liquid travel along the sensor has occurred to generate power, indicating that the sensor is ready for use. If when the sensor has been shown to be powered an inconclusive result has been obtained further indicator means can inform the user to either apply more liquid sample to the sensor or to wait for a longer time until the liquid can travel along the assay strip to the detection electrodes.

The electrochemical detection arrangement preferably comprises detection electrodes for an amperometric, a potentiometric or a coulometric detector.

An amperometric detector determines the amount of a substance by means of an oxidation-reduction reaction involving that substance. Electrons are transferred as a part of the reaction, so that the electrical current through the detector is related to the amount of the substance seen by the detector.

A potentiometric detector is a chemical detector that measures the concentration of a substance by determining the electrical potential between a specially prepared surface and a solution containing the substance being measured. A coulometric detector detects differences in charge.

Preferably, the electrochemical detection arrangement is printed onto the substrate as a printed circuit board (PCB). Preferably, the detection electrodes are also printed onto the substrate.

The presence of a species under test may be determined by the sensor either directly or indirectly. By directly detectable we mean that it is the species itself that is detected at the electrochemical detection arrangement. Examples of directly detectable species include metals, for example from soil or water samples. The conductive properties of metals will directly provide a change in potential when presented to the electrochemical detection arrangement.

By indirectly detectable we mean that the species is labelled with an electrochemically detectable label. The sensor may for example be used to detect the levels of analyte in a biological sample and in which case the sensor is essentially as disclosed in our co-pending U.K. patent applications, number 9813721.9 and number 9822076.7 (see PCT/GB99/02022) and includes the power source according to the sensor device of the present invention.

To detect the levels of an analyte in a biological sample the analyte may be specifically labelled. Labelling of the species under test may be effected by supplying a binding partner specific for an analyte that may be present in the sample. This specific binding partner has a label that is either directly or indirectly detectable by the electrochemical detection arrangement.

The sensor apparatus may be arranged such that only electrochemically detectable label that has resulted directly or indirectly from the analyte binding to a reagent specific for that analyte is measured by the electrochemical detection arrangement. Unbound analyte, label free in solution or labelled or unlabelled specific binding partner that has not bound analyte are not detected.

Examples of specific binding partners for an analyte include specific antibodies, antigens, receptors for the analyte, for example if the analyte is a hormone the specific binding reagent may be its receptor, enzymes which bind the analyte, any other protein capable of recognising and binding to the analyte or a non-proteinaceous compound having analyte binding capacity.

Preferred directly electrochemically detectable labels are electroactive species that promote a change in potential at the electrochemical detection arrangement. Examples of electroactive species which may directly change the potential at the electrochemical detection arrangement are metals and metal ions, such as sodium, lead, aluminium and potassium, as well as calcium ions, hydrogen ions, fluoride ions and ammonium ions. The conductive properties of metals will directly provide a change in potential when present at the electrochemical detection arrangement.

Examples of electroactive species which may indirectly change the potential at the electrochemical detection arrangement are those that undergo redox reactions, for example hydrogen peroxide may generate hydrogen ions which may change the potential at the electrochemical detection arrangement. Preferred indirectly electrochemically detectable labels are reagents that induce at least one reaction at a reaction region that produce a species that is directly or indirectly electrochemically detectable. A preferred indirectly electrochemically detectable label is an enzyme which catalyses a reaction at a reaction region on the substrate which produces a species which is directly or indirectly electrochemically detectable. To reduce artificial results from being generated, only indirect label due to analyte binding to specific binding partner is able to reach the reaction region.

The enzyme label preferably catalyses one reaction that produces a species that is electrochemically detectable label or may initiate a cascade of reactions which at a point in the cascade produces a species that is electrochemically detectable label. An example of an enzyme which is a suitable indirectly electrochemically detectable label is the enzyme P1 nuclease. P1 nuclease initiates a cascade reaction that activates the enzyme glucose oxidase to catalyse the reaction of glucose to gluco 1,5, lactone with the release of hydrogen peroxide. The levels of hydrogen peroxide generated may be indirectly measured by the electrochemical detection arrangement. Alternatively, horseradish peroxidase may also be present and this may catalyse the reduction of hydrogen peroxide to water by reductant, the water also being indirectly detectable at the electrochemical detection apparatus.

An advantage of using P1 nuclease as an indirectly electrochemically detectable label is that the cascade reaction initiated by P1 nuclease amplifies the effect of the presence of analyte at the electrochemical detection apparatus by up to $10^6$ times. This allows low levels of analyte in a sample to be detected.

A typical embodiment of the invention is an electrochemical sensor incorporated in a hollow liquid-impermeable casing, the sensor communicating directly or indirectly with the exterior of the casing such that a liquid sample may be applied to the sample application region of the sensor.

An important preferred embodiment of the present invention is the choice of nitro-cellulose as the substrate. Nitro-cellulose is readily available in a range of pore sizes and this facilitates the selection of a substrate to suit requirements such as sample flow rate.

Preferably. the substrate has a pore size of at least one micron. Preferably, the substrate has a pore size of not greater than about 20 microns. Generally a substrate having a pore size of between about 8–12 microns is preferred. It is preferable that the flow rate of the sample through the carrier should be at a rate of 1 cm in not more than 2 minutes but slower flow rates may be used if desired.

The electrochemical sensor apparatus according to the present invention may be used to determine a wide variety of species. The species can be, for example a metal, mineral or chemical. such as pesticides or may be biological, for example a virus, protein or other analyte. The analytes can be, for example, proteins, antigens, immunoglobulins, viruses, hormones, polynucleotides, drugs, steroids and infectious agents, for example infectious agents of bacterial origin such as Chlamydia, Streptococcus. The sensor apparatus may be used biologically to diagnose diseases, genetic mutations causing a pre-disposition to a disease and alcohol or drug abuse. The sensor may also be used environmentally to determine the levels of metal, minerals or chemicals in rivers, streams or soil, for example.

The invention will be further described by way of example only with reference to the accompanying drawings in which.

Figure 1:
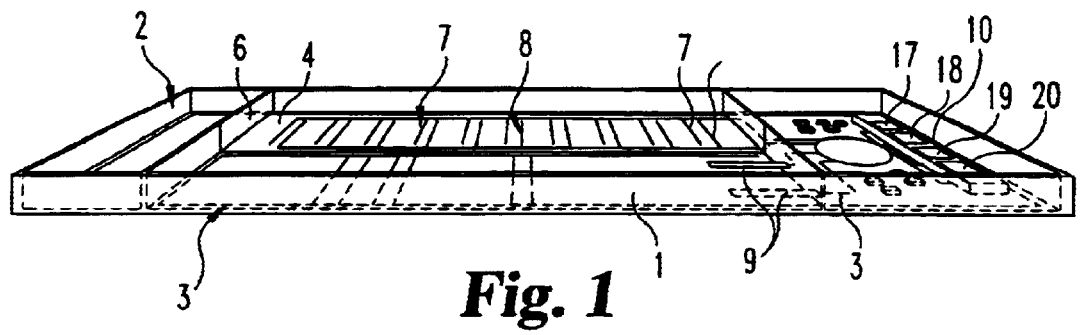
FIG. 1 is a schematic perspective view of a first embodiment of a sensor apparatus in accordance with the present invention.
Figure 2:
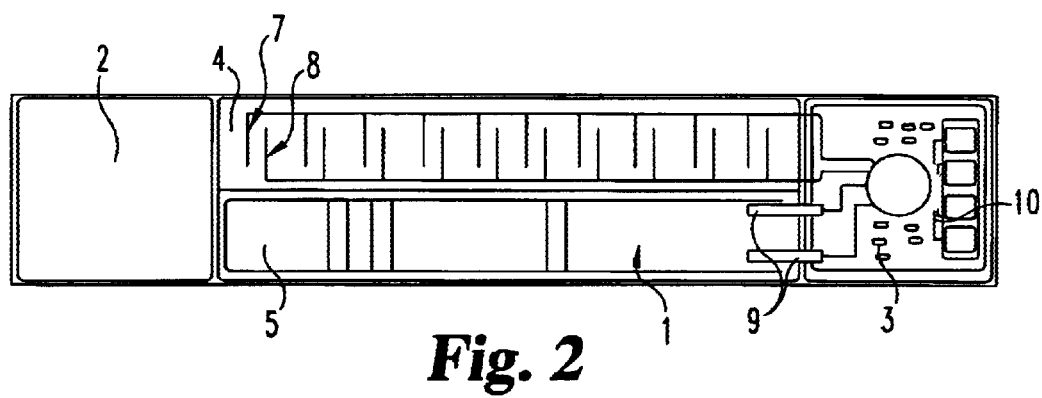
FIG. 2 is a schematic plan view of a first embodiment of a sensor apparatus in accordance with the present invention.

As shown in FIGS. 1 and 2, an electrochemical sensor in accordance with the invention comprises a chromatographic substrate 1 provided at one end with a sample application region 2 and at the opposite end with an electrochemical detection arrangement 3. Between the sample application region 2 and the electrochemical detection arrangement 3. the substrate 1 is sub-divided longitudinally into two parallel liquid travel tracks 4 and 5, separated by a plastics barrier 6.

Travel track 4 is provided with an electrode arrangement comprising two electrodes 7 and 8. each extending substantially along the entire length of the track 4. The electrodes 7 and 8 are of dissimilar materials and each comprises a plurality of fingers which are interdigitated with those of the other electrode. At the downstream end of the travel track 4. the electrodes 7 and 8 are electrically associated with the electrochemical detection arrangement 3 and, as described more fully below, provide a power source therefor.

Travel track 5 is an "assay" track and is provided at the downstream end thereof with a pair of detection electrodes 9 capable of detecting electrochemically detectable species. The detection electrodes 9 are electrically associated with the electrochemical detection arrangement 3.

In use of the electrochemical sensor, liquid sample to be analysed is applied to the sample application region 2 and travels along both liquid travel tracks 4 and 5. Liquid travel along travel track 4 provides an electrochemical pathway between the electrodes 7 and 8, with consequent "in situ" generation of an electrochemical cell which provides a power source for operating the electrochemical detection arrangement 3.

The illustrated device incorporates an indicator display arrangement 10 linked via electronic circuitry to the electrodes 7 and 8 and to the detection arrangement 3.

In FIGS. 1 and 2 the indicator display 10 comprises a coloured light 17. Illumination of the light 17 indicates that the liquid sample has travelled far enough along the travel track 4 for the power source to generate sufficient current to run the sensor.

Further illumination display means may be provided to indicate the test results. Such illumination display means may comprise a text message, or preferably, as shown in FIGS. 1 to 4 may comprise a traffic light display of three lights 18, 19 and 20, one of which is illuminated dependent upon the test results. Light 18 is coloured green and its illumination indicates that the test gave a positive result, light 19 is coloured amber and its illumination indicates that the test results were inconclusive and the test should be continued and light 20 is coloured red and its illumination indicates that the test gave a negative result.

Figure 3:
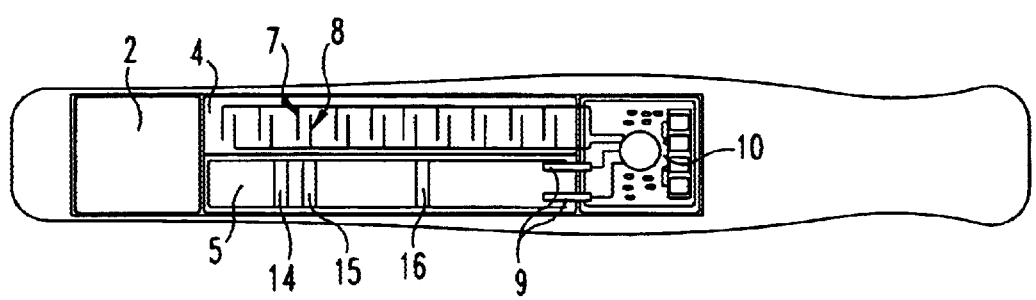
FIG. 3 is a schematic view of a first embodiment of a sensor apparatus in accordance with the present invention in a casing.
Figure 4:
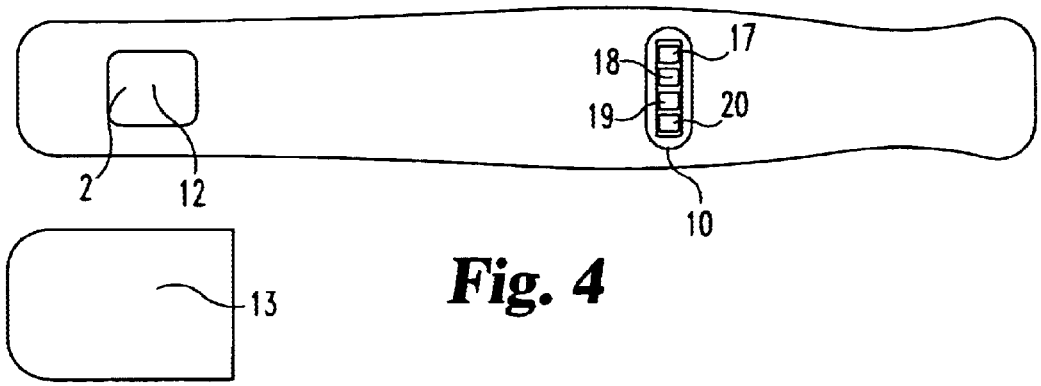
FIG. 4 is a schematic view of the exterior of the casing shown in FIG. 3.

As shown in FIGS. 3 and 4 an electrochemical sensor in accordance with a preferred embodiment of the invention is incorporated into a casing 11 which has an aperture 12 above the sample application region 2 and an aperture 13 above the indicator means 10. The electrochemical sensor further has a cap 14 for fitting over the casing 11 to cover the aperture 12 when the electrochemical sensor is not in use.

With reference to FIG. 3, an electrochemical sensor in accordance with a preferred embodiment the present invention will be described in use below.

The electrochemical sensor described with reference to FIG. 3 is arranged to detect the presence of an indirectly electrochemical analyte in a biological sample. In this arrangement the assay track 5 comprises, in the direction of fluid flow from the sample application region 2 to the electrochemical detection arrangement 3, in longitudinal spaced arrangement, a first region 14, a second region 15 and a third region 16, each region extending across the entire width of the assay track 5. The spatial separation along travel track 5 between regions 14, 15 and 16 can be of any length as long as the regions are separated.

The first region 14 is printed or impregnated with a specific anti-analyte antibody which is labelled with P1 nuclease (an enzyme). P1 nuclease itself is not electrochemically detectable. The second region 15 is printed or impregnated with an anti-anti-analyte antibody-which only binds free labelled anti-analyte antibody. The third region 16 comprises an enzyme site comprising all the substrates and enzymes (except P1 nuclease) necessary for a cascade reaction whose initial reaction is catalysed by P1 nuclease.

In use a liquid sample is applied to an electrochemical sensor as shown in FIG. 4 through the aperture 12 such that the liquid is soaked up on the absorbent pad of the sample application region 2. The liquid sample then migrates along the substrate travel tracks by capillary action.

As the liquid of the sample migrates along travel track 4, it moistens the previously dry substrate and allows current to flow from the interdigitated electrodes 7 and 8 towards the electrochemical detection arrangement 3. When sufficient current is supplied to the electrochemical detection arrangement 3 this causes the electronic circuit to cause illumination of light 17 of the indicator display.

The migration of the sample along the assay track 5 moistens the previously dry substrate and draws with it dissolved or dispersed reagents present on the track 5. Analyte in the sample binds at the first region 14 with a specific anti-analyte antibody that is labelled with P1 nuclease (an enzyme). P1 nuclease itself is not electrochemically detectable. As the liquid is drawn along the track 5 it draws the analyte bound labelled specific antibody to the second region 15. At the second region 15 the analyte bound labelled specific antibody will bind to anti-anti-analyte antibody which only binds free labelled analyte bound antibody to form a labelled complex. Continued migration along the track 5 draws the labelled complex to the third region 16 which comprises an enzyme site comprising all the substrates and enzymes (except P1 nuclease) necessary for a cascade reaction whose initial reaction is catalysed by P1 nuclease. When this occurs, the cascade reaction catalysed by P1 nuclease can occur resulting in the production of hydrogen peroxide which may be detected at the detection electrodes 9.

The amount of hydrogen peroxide present at the test electrodes 9 is interpreted by the electronic circuitry and causes illumination of one of the three coloured lights 18, 19, and 20 of the illumination display means dependent upon the test results.

Although the example refers to the detection of an analyte which is itself indirectly electrochemically detectable it is also envisaged that the electrochemical sensor may be used to detect electrochemically detectable species such as metals. In such an arrangement, the assay track need not comprise any of the three regions 14, 15 or 16 as the species to be detected will be directly detectable at the detection electrodes 9 and this will be indicated provided that sufficient flow of sample has occurred to power the electrochemical detection arrangement.

What is claimed is:

1. An electrochemical sensor for a liquid sample, the sensor comprising a substrate along which a liquid sample may travel by capillary action, said substrate being associated with an electrochemical detection arrangement and a power source therefor, wherein the power source comprises at least one pair of electrodes of dissimilar material provided on the substrate and arranged such that liquid sample will travel by capillary action between the pairs of electrodes of said at least one pair of electrodes causing a current to be generated by said power source for operating the electrochemical detection arrangement.

2. An electrochemical sensor as claimed in claim 1 in which said at least one pair of electrodes separately comprise carbon, or one or more metals.

3. An electrochemical sensor as claimed in claim 1 in which said at least one pair of electrodes separately comprises copper and zinc.

4. An electrochemical sensor according to claim 1 in which one or more of said at least one pair of dissimilar materials are interdigitated such that current, in the presence of liquid, may flow from one electrode to the other electrode of the electrode pair.

5. An electrochemical sensor according to claim 1 comprising a first liquid travel track provided over at least part of the length of said substrate upon which said power source is formed comprising interdigitated electrodes of dissimilar materials, and a second liquid travel track also provided over at least part of the length of said substrate, the downstream end of the second track being provided with a detection electrode arrangement associated with the electrochemical detection arrangement.

6. An electrochemical sensor according to claim 5 in which said first and second liquid travel tracks are separated by a liquid impermeable barrier.

7. An electrochemical sensor according to claim 1 further comprising indicator means.

8. An electrochemical sensor according to claim 7 in which the indicator means comprises a liquid crystal display.

9. An electrochemical sensor according to claim 1, in which the substrate comprises one or more reagents which in the presence of the species under test induce a reaction that produces a species that is directly or indirectly electrochemically detectable at the electrochemical detection arrangement.

* * * * *